United States Patent [19]

Cote et al.

[11] Patent Number: 5,889,179
[45] Date of Patent: Mar. 30, 1999

[54] BACTERIA AND ENZYMES FOR PRODUCTION OF ALTERNANT FRAGMENTS

[75] Inventors: Gregory L. Cote, Edwards; Herbert Wyckoff, Washington, both of Ill.

[73] Assignee: The United States of America, as represented by the Secretary of Agriculture, Washington, D.C.

[21] Appl. No.: 98,368

[22] Filed: Jun. 17, 1998

Related U.S. Application Data

[62] Division of Ser. No. 490,003, Jun. 12, 1995, Pat. No. 5,786,196.
[51] Int. Cl.$^6$ ....................................................... C07H 1/00
[52] U.S. Cl. .................................. 536/123.1; 536/123.12; 435/72; 435/98; 514/61
[58] Field of Search ........................... 536/123.1, 123.12; 514/61; 435/72, 98

*Primary Examiner*—Leon B. Lankford, Jr.
*Attorney, Agent, or Firm*—M. Howard Silverstein; Randall E. Deck; John D. Fado

[57] ABSTRACT

A new enzyme, alternanase, which is effective for the endo-hydrolytic cleavage of alternan, producing a thinned composition of low molecular weight fractions which exhibit reduced viscosity and increased solubility relative to native alternan, is described. The enzyme is produced and secreted extracellularly by a plurality of novel bacteria isolated from soil. One of the fractions present in the thinned alternan resulting from hydrolysis with alternanase is a the cyclic tetrasaccharide, cyclo{-6)-$\alpha$-D-Glcp-(1,3)-$\alpha$-D-Glcp-(1,6)-$\alpha$-D-Glcp-(1,3)-$\alpha$-D-Glcp-(1-}. A novel method for isolating strains of microorganisms which produce endo-$\alpha$-D-glucanases such as alternanase effective for the endo-hydrolytic cleavage or thinning of alternan is also described. Cultures of the subject strains are contacted with a test substrate of alternan coupled to a detectable indicator. Detection of released indicator provides an indication of endo-$\alpha$-D-glucanase activity.

5 Claims, No Drawings

BACTERIA AND ENZYMES FOR PRODUCTION OF ALTERNANT FRAGMENTS

This application is a division of application Ser. No. 08/490,003, filed Jun. 12, 1995, now U.S. Pat. No. 5,786, 196. The contents of which are incorporated by reference herein.

BACKGROUND OF THE INVENTION

1. Field of Invention

This invention relates to bacteria and enzymes effective for hydrolyzing alternan to lower molecular weight fragments having reduced viscosity.

2. Description of the Prior Art

The polysaccharide alternan was first described by Jeanes et al. (1954, *J. Am. Chem. Soc.*, 76:5041–5052) as one of two extracellular α-D glucans, referred to as fraction S, produced by *Leuconostoc mesenteroides* NRRL B-1355. The structure of this fraction was later determined by Misaki et al. (1980, Carbohydr. Res., 84:273–285) to consist primarily of an alternating sequence of α-1,3-linked and α-1,6-linked D-glucose residues, with approximately 10% branching. Because the α-1,3-linkages are part of the linear chain of the S fraction and there are not any consecutive α-1,6-linkages, the fraction is not a true dextran, and Cote and Robyt (1982, *Carbohydr. Res.*, 101:57–74) therefore named this fraction alternan. These authors also isolated the enzyme alternansucrase which synthesizes alternan from sucrose.

Native, high-molecular weight alternan may be produced fermentatively as described by Jeanes et al. (1954, ibid) or enzymatically as described by Cote and Robyt (1982, ibid). This compound, its low molecular weight derivatives produced by sonication, and limit alternan produced by hydrolysis with the isomalto($G_2$)-dextranase of *Arthrobacter globiformis* T6 (Misaki et al., 1980, ibid), have properties resembling certain functional characteristics of gum arabic, maltodextrins, or Polydextrose (Cote, 1992, *Carbohydrate Polymers*, 19:249–252). The low viscosities of these products lend themselves to potential commercial applications as substitutes for gum arabic, for use as bulking agents and extenders in foods and cosmetics, particularly as noncaloric, carbohydrate-based soluble food additives in artificially sweetened foods.

Although alternan is an α-D-glucan, no endo-hydrolytic enzymes have been described which are capable of hydrolyzing alternan to any great extent (Cote, 1992, ibid). Misaki et al. (1980, ibid) reported that an endo-dextranase from a Penicillium species hydrolyzed alternan to a small degree, 7.3%. However, in subsequent work, Cote and Robyt (1982, ibid) examined the effect of this and other endo-dextranases upon alternan and found that the enzymes were unable to hydrolyze alternan, and no measurable low molecular weight products were produced. This lack of activity was not surprising, because the endo-dextranases are specific for dextrans, requiring consecutively linked α-1,6-D-glucose residues as substrates, while alternan is composed of alternating α-1,3- and α-1,6-linkages.

In contrast to what one may expect, alternan is considerably resistant to microbial degradation and is also not attacked by enzymes that degrade starch, nigeran or pullulan (Cote, 1992, ibid). The only enzymes that have been reported to hydrolyze alternan to any significant extent are isomaltodextranases, which are not endo-hydrolases but rather exo-hydrolases or exo-dextranases. Two isomaltodextranases were examined for hydrolysis of alternan (referred to as B-1335 fraction S), the isomaltodextranases produced by *Arthrobacter globiformis* (Sawai et al., 1978, *Carbohydrate Res.*, 66:195–205) and by an actinomycete Actinomadura (Sawai et al., 1981, *Carbohydrate Res.*, 89:289–299). The authors concluded that the isomaltodextranases release mainly isomaltose units from the non-reducing ends of alternan chains that are terminated with an α-1,6-linked D-glucopyranosyl residues.

Although there is firmer evidence for exo-action of the Actinomadora isomaltodextranase (Sawai et al., 1981, ibid), the information on the mode of action of the *A. globiformis* enzyme is not so straightforward. Its alternan digest also contained, besides isomaltose, some larger oligosaccharide fragments, identified by Sawai et al. (1981, ibid) as α-D-Glcp-(1,6)-α-D-Glcp-(1,3)-α-D-Glcp-(1,6)-α-D-Glc, and α-D-Glcp-(1,3)-α-D-Glcp-(1,6)-α-D-Glcp-(1,3)-α-D-Glcp-(1,6)-D-Glc. The authors suggested that these larger products represented either fragments that originated in the reducing-end terminals remaining after an exo-pattern of alternan digestion or, they were transisomaltosylation products. The second alternative finds support in the fact that isomaltodextranase is a glycanase retaining the anomeric configuration of attacked linkages in the hydrolysis products (Sawai & Niwa, 1975, *Agr. Biol. Chem.*, 39:1077–1083). The *A. globiformis* isomaltodextranase has also been shown to cleave all types of α-glucopyranosyl linkages following an isomaltosyl unit towards the reducing end of the substrate. In other words, the enzyme liberates terminally linked isomaltose whether the linkage is α-1,6-, α-1,4-, α-1,3- or α-1,2- (Torii et al., 1976, *Biochem. Biophys. Res. Comm.*, 70:459–464).

The recent observation by Okada et al. (1988, Agr. Biol. Chem, 52:829–836) that *A. globiformis* isomaltodextranase is capable of attacking pullulan in an endo-fashion cleaving the α-1,4-linkages following the α-1,6-linkage, raised again the question concerning the exo- or endo-character of the enzyme. However, studies with *A. globiformis* isomaltodextranase purified in this laboratory according to Okada et al. (1988, Agric. Biol. Chem., 52:495–501) have confirmed that the enzyme is not capable of endo-hydrolytic cleavage of alternan, but functions in an exo- fashion.

SUMMARY OF THE INVENTION

We have now discovered a new enzyme, alternanase, which is effective for the endo-hydrolytic cleavage of alternan, producing a thinned composition of low molecular weight fractions which exhibit reduced viscosity and increased solubility relative to native alternan. Alternanase is an endo-α-D-glucanase specific for alternan, having substantially greater activity toward alternan than dextran. The enzyme is produced and secreted extracellularly by a plurality of novel bacteria which we have isolated from soil. Among the fractions present in the thinned alternan resulting from hydrolysis with alternanase are a novel cyclic tetrasaccharide, cyclo{-6)-α-D-Glcp-(1,3)-α-D-Glcp-(1,6)-α-D-Glcp-(1,3)-α-D-Glcp-(1-} and derivatives thereof.

The invention also relates to a novel method for isolating strains of microorganisms which produce endo-α-D-glucanases such as alternanase effective for the endo-hydrolytic cleavage or thinning of alternan. Cultures of the subject strains are contacted with a test substrate, generally alternan coupled to a detectable indicator, which is specific for endo-acting glucanase. Detection of released indicator provides evidence of endo-α-D-glucanase activity.

In accordance with this discovery, it is an object of this invention to provide a novel enzyme for thinning alternan by endo-hydrolysis.

Another object of this invention is to provide a composition of thinned alternan, composed of novel low molecular weight fractions, for use as bulking agents and extenders in foods and cosmetics, especially as carbohydrate-based soluble food additives.

Yet another object of this invention is to provide isolated strains of microorganisms which produce and secrete enzymes effective for the endo-hydrolysis of alternan, as well as a method for isolating such microorganisms.

Other objects and advantages of this invention will become obvious from the ensuing description.

DETAILED DESCRIPTION OF THE INVENTION

The enzyme of this invention, designated alternanase, is an endo-α-D-glucanase which is effective for the endo-hydrolytic cleavage of alternan. Alternanase is specific for alternan, hydrolyzing alternan or polysaccharides which possess D-glucose residues linked in an alternating α-1,3- and α-1,6-fashion. In contrast, the rate and extent of hydrolytic activity of alternanase toward other polysaccharides and particularly dextran, which is defined herein in the manner described by Mahoney et al. (U.S. Pat. No. 5,217,620) as those polysaccharides having backbones primarily comprised of α-1,6-linked D-glucose residues, are generally insignificant (Biely et al., 1994, Eur. J. Biochem., 226:633–639, the contents of which are incorporated by reference herein). Therefore, the enzyme is not a dextranase. When measured as reducing sugars released over time as described by in Example 3, the initial rate of hydrolysis of alternan by alternanase is 100%, while the initial rates of hydrolysis of dextrans are less than 1%. Similarly, no substantial hydrolytic action is displayed toward starch, nigeran, or the soluble glucans from *Streptococcus sobrinus*, and only poor hydrolytic activity is displayed toward pullulan.

Alternanase was originally isolated from soil bacteria that were selected for the ability to produce extracellular enzymes which hydrolyzed alternan in an endo-fashion. Using the screening procedure described in greater detail hereinbelow, seven strains of soil bacteria have been isolated which produce and secrete extracellular alternanase. All seven strains have been deposited under the Budapest Treaty in the United States Department of Agriculture, Agricultural Research Service culture collection in Peoria, Ill., and have been assigned deposit numbers NRRL B-21189, B-21190, B-21191, B-21192, B-21193, B-21194 and B-21195. Of these, strain NRRL B-21195 produces the highest level of alternanase activity and is preferred. All seven strains have been presumptively identified as belonging to the genus Bacillus.

Alternanase obtained from any of the above-mentioned strains hydrolyze alternan in the same manner. Regardless of the source, the enzymes endo-hydrolytically cleave alternan to produce the same fragments and particularly the same oligosaccharides. When analyzed by thin-layer chromatography, the oligosaccharides prepared from alternanase from the different strains all produce identical patterns. However, some minor differences are evident between the enzyme isolated from these different strains. Polyacrylamide gel electrophoresis (PAGE) of the crude enzymes, followed by activity staining, indicates that there are differences in the ionic charges and/or molecular weights of the enzymes.

Production of alternanase may be accomplished by culture of any of the aforementioned bacterial strains, isolates or subcultures having the identifying characteristics of those strains, mutants of those strains capable of producing alternanase, or other isolates recovered by the screening procedure described hereinbelow, by conventional techniques under aerobic conditions that are effective to promote growth and alternanase production. Any number of well-known liquid or solid culture media may be used, although growth on liquid media is preferred as the enzyme is secreted into the media and recovery is simplified. Without being limited thereto, particularly preferred culture media include Brain-Heart Infusion Broth (Difco, Inc., Detroit, Mich.) or Tryptic Soy Broth. Similarly, the media may contain a variety of carbon sources which will support growth and production of the enzyme, including but not limited to glucose, starch, maltose and alternan. The presence of alternan in the culture medium is not essential for production of the enzyme, although optimal alternanase production is achieved by addition of alternan thereto. The precise degree of enhancement is variable and is dependent upon the particular strain used. For example, production of the enzyme is greatly increased by addition of alternan when using strains NRRL B-21189, B-21190, B-21191, B-21192, B-21193 and B-21194. In contrast, strain B-21195 is a constitutive producer of alternanase, and addition of alternan effects a less dramatic increase in alternanase production, approximately between 20 to 30%. The amount of alternan added to the media is not critical and may be readily determined by the practitioner skilled in the art. The bacteria will grow and produce alternanase over wide pH and temperature ranges, with a pH of about 7.0 and a temperature of about 30° C. being preferred.

Upon completion of the fermentation, typically between 24 to 96 hours, alternanase may be isolated or separated from the microorganisms using techniques conventional in the art, such as by centrifugation or filtration. As a practical matter, it is envisioned that commercial formulations of alternanase may be prepared directly from liquid culture medium from which cells have been removed in this manner, thereby obviating the need to further purify the enzyme.

Optionally, the alternanase remaining in the culture medium may be further concentrated and purified, particularly for applications demanding a high degree of purity where contamination by other enzymes, microbial products, monosaccharides, or culture media components may be undesirable. Suitable techniques for concentration and/or purification of alternanase may be readily determined by the practitioner skilled in the art and include, for example, dialysis, ion-exchange chromatography, and preferably HPLC size-exclusion chromatography and electrophoresis, particularly polyacrylamide-gel-electrophoresis (PAGE). Using these techniques, alternanase may be recovered in pure or substantially pure form. It is also envisioned that the enzyme may be formulated in conjunction with a suitable inert carrier or vehicle as known in the art. The skilled practitioner will recognize that such carriers must be compatible with the enzyme. Without being limited thereto, details of the preferred fermentation and separation procedures are described in Example 3 and in Biely et al. (1994, Eur. J. Biochem., 226:633–639, the contents of which have been incorporated by reference hereinabove).

Treatment of alternan with alternanase reduces the viscosity of aqueous alternan solutions and results in the formation of a series of low-molecular weight oligosaccharides. As the starting material, alternan may be prepared by conventional fermentation or enzymatic reaction. Suitable processes for producing alternan are known in the art and include, but are not limited to, fermentation with *Leuconos-* toc mesenteroides NRRL B-1355, B-1498, or B-1501 as described by Jeanes et al. (1954, *J. Am. Chem. Soc.*, 76:5041–5052, the contents of which are incorporated by reference herein), or reaction of sucrose with alternansucrase as described by Cote and Robyt (1982, *Carbohydr. Res.*, 101:57–74, the contents of which are incorporated by reference herein).

In use, a catalytically effective amount of alternanase may be contacted with alternan in an aqueous solution under conditions effective to hydrolyze the polysaccharide. Alternanase generally retains endo-hydrolytic activity over pH and temperature ranges between about 4.5 to 9 and about 0° to at least 50° C., respectively, with optima at about pH 7 and about 40° C. for the enzyme from strain NRRL B-21195. At a pH of 7.0, enzyme activity decreases rapidly as the temperature is increased to 60° C. The presence of calcium ions in the reaction mixture is required for optimal activity. Addition of the calcium binding agent EDTA has been found to inhibit activity.

The reduced viscosity product resulting from the hydrolysis of alternan with alternanase is composed of a series of both reducing and non-reducing, low-molecular weight oligosaccharides. The actual degree of alternan hydrolysis, that is the degree of depolymerization, and hence the final viscosity of the solution, may be readily controlled by terminating the reaction at any time during the reaction. A variety of techniques which are conventional in the art may be used to stop the reaction, including heating to denature the enzyme, addition of inhibitors (e.g., EDTA), or adjusting the pH.

Because some of the oligosaccharide products may inhibit the enzyme, hydrolysis of alternan may be carried to completion more rapidly by removing low-molecular weight products from the reaction mixture. For example, without being limited thereto, the low-molecular weight fractions may be removed by dialysis. In any event, in accordance with the preferred embodiment, the starting alternan solution is hydrolyzed for a sufficient time until the viscosity has been reduced at least about 10%.

The predominant oligosaccharides resulting from the hydrolytic reaction are larger than disaccharides, and exhibit high solubility in water and very low viscosity relative to native alternan. When reacting with purified alternanase, neither glucose nor nigerose are produced. However, contamination with α-glucosidase, which may be present in crude preparations of the enzyme, does result in the production of glucose.

Following separation by thin-layer chromatography, at least seven saccharide products may be recovered (excluding glucose); other saccharides of higher degree of polymerization are also produced. The oligosaccharide formed in the greatest proportion is a novel cyclic tetrasaccharide of D-glucosyl residues linked in an alternating α-1,3-α-1,6-fashion. This cyclic tetrasaccharide has been identified as cyclo{-6)-α-D-Glcp-(1,3)-α-D-Glcp-(1,6)-α-D-Glcp-(1,3)-α-D-Glcp-(1-} and has the following structure:

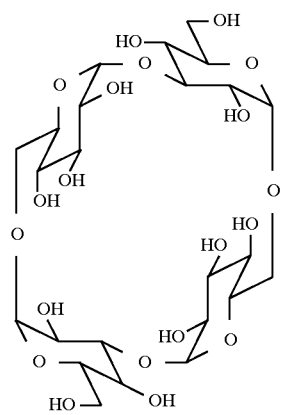

This structure is intended to show linkage only, and no particular conformation is implied. The compound is produced upon reaction with alternanase derived from any of the above-mentioned bacterial isolates. Other saccharides formed upon reaction with alternanase include isomaltose, a reducing trisaccharide identified as α-D-glucopyranosyl-1,3-α-D-glucopyranosyl-1,6-α-D-glucose, and four other relatively minor higher molecular weight oligosaccharides. One of latter mentioned group has been tentatively identified as a glucosylated cylic tetrasaccharide having a single D-glucopyranosyl unit attached to the O6 of one of the 3-O-glucosylated ring residue as shown by the following structure:

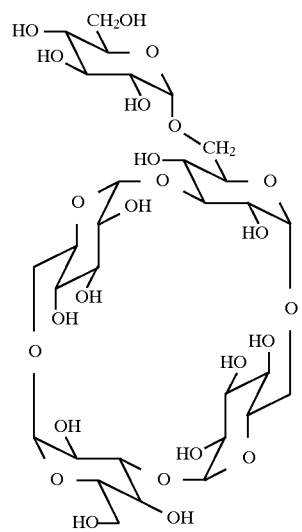

A thorough description of the reaction of alternan with alternanase, the reaction products, and their separation, is described by Cote and Biely (1994, Eur. J. Biochem., 226:641–648, the contents of which are incorporated by reference herein).

While the mechanism of action of alternanase has not been completely discerned, the enzyme is specific for alternan and apparently cleaves the α-1,3-linkages that occur adjacent to, or are flanked by α-1,6-linkages. Therefore, an equivalent systematic name for alternanase may be α-1,3 (6)-glucan glucanohydrolase. Without being bound by theory, based upon the structure of the cyclic tetrasaccharides, it is envisioned that the enzyme cleaves the helical alternan chain at every fourth glycosidic linkage (i.e. every other α-1,3-linkage).

For commercial applications, the reduced viscosity complex solution of hydrolyzed alternan produced from treatment with alternanase may be used directly or, in the alternative, the low-molecular oligosaccharides may be separated for individual use. Again, suitable techniques for separation and purification of the oligosaccharides include, for example, thin-layer chromatography. In either event, hydrolyzed alternan may be used in a variety of applications, particularly as bulking agents or extenders in foods and cosmetics. Most notably, because they are not readily digested and are not subject to non-enzymatic browning, either the complex solution of hydrolyzed alternan or the separated oligosaccharide fragments, may be used as soluble, low- or non-caloric sucrose substitutes. It is also envisioned that the products may be used as complexing agents similar to cyclodextrins, and as inhibitors of certain antigen-antibody binding and lectin-carbohydrate binding systems. Derivatives of the oligosaccharides, and particularly the cylic tetrasaccharides, may be useful in binding and complexing metal salts. Without being limited thereto, preferred derivatives include O-alkyl ethers, O-acyl esters, partially or fully sulfated esters, and particularly ionic carboxymethyl and diethylaminoethyl derivatives. These derivatives may be prepared at one or more sites on the cyclic oligosaccharides using techniques conventional in the art, such as described by Yalpani (1988, Polysaccharides: Syntheses, Modifications and Structure/Property Relations, Elsevier Press, New York, pages 234–299) or Kennedy and White (Bioactive Carbohydrates: In Chemistry, Biochemistry and Biology, Halsted Press, New York, pages 63–65), the contents of each of which are incorporated by reference herein.

This invention also relates to a novel process for screening and isolating microorganisms and bacteria effective for the production of alternanase. The process may be used for screening microorganisms from a variety of different sources, including, but not limited to naturally occurring strains, purified isolates, their clones or mutants, or any microbial transformants that have been transformed with an expression vector incorporating foreign genetic material.

In accordance with this method, the test microorganisms are first cultured on conventional nutrient media under conditions suitable for growth thereof. The skilled practitioner will recognize that the particular media and conditions selected will vary with the test microorganism of interest and may be readily determined. However, when screening naturally occurring soil isolates, the microorganisms are preferably cultured aerobically at about 30° C. on Brain-Heart Infusion Broth or Tryptic Soy Broth containing alternan as a carbon source. Following incubation, either the resultant culture of the test microorganism, or the spent culture fluid from which cells have been removed, are contacted with a test reagent which is specific for alternanase. For use herein, the test reagent is composed of alternan coupled to a detectable indicator which is released upon endo-hydrolysis of the polysaccharide. Preferred test reagents include alternan coupled to a chromogen, particularly Remazol-brilliant blue-alternan (RBBA). Preparation of RBBA is described in Example 1 hereinbelow. Detection of release of the indicator demonstrates production of alternanase activity by the test microorganism. In a preferred embodiment, the test reagent, RBBA, may be incorporated into a nutrient medium agar onto which the culture of the test microorganism is streaked and incubated. Those microorganisms which produce clearing zones in the blue-dyed agar medium are positive for alternanase activity.

The following examples are intended only to further illustrate the invention and are not intended to limit the scope of the invention which is defined by the claims.

EXAMPLE 1

Test media

For use herein, microorganisms were screened for alternanase activity using an agar test medium containing alternan coupled to the chromophore Remazol-brilliant blue (Sigma Chemical Co.).

Alternan was prepared from sucrose enzymically by use of alternansucrase of *Leuconostoc mesenteroides* NRRL B-1355 as described by Cote and Robyt (1982, *Carbohydr. Res.*, 101:57–74). The Remazol-brilliant blue-alternan conjugate (RBBA) was prepared following the procedure described by Rinderknecht et al. [1967, *Experientia* (Basel), 23:805, the contents of which are incorporated by reference herein] for the preparation of covalently dyed amylose. Briefly, 50 g of alternan was suspended in 500 ml of water with stirring at 50° C. A solution of 5.0 g of Remazol-brilliant blue in 500 ml of water was added. Sodium sulfate (100 g) was then added in several portions over the next 45 minutes. Trisodium phosphate (5.0 g in 50 ml water) was then added to the reaction mixture, and the mixture continuously stirred at 50° C. for an additional 75 minutes. The RBBA product was precipitated by two volumes of ethanol, dialyzed to remove residual unreacted dye, and lyophilized. The dye content in the conjugate was 3.5% as determined photometrically ($\epsilon_{595}=9.25\times10^3$ $M^{-1}$ $cm^{-1}$).

The test media for detecting alternanase activity were prepared by incorporating 0.5% of the RBBA conjugate and 1.5% agar into each of the following media: Tryptic Soy Broth, YEPD, LB, Dex-10, or PMN. The contents of these media are as follows:

LB Medium (Miller, 1972, Experiments in Molecular Genetics Cold Spring Harbor Lab., Cold Spring Harbor, N.Y.):
  tryptone 10 g
  yeast extract 5 g
  NaCl 10 g
  water 1 L
  pH 7.5

PMN Broth (Mitchell and Gilliland, 1983, J. Dairy Sci., 66:712–718):
  PMN 50 g
  glucose 20 g
  Primatone 20 g
  yeast extract 1 g
  Tween 80 1 g
  water 1 L YEPD Medium (McKay, 1991, Lett. Appl. Microbiol., 13:265–267):
  yeast extract 5 g
  protease peptone 10 g
  glucose 10 g
  ammonium sulfate 2 g
  water 1 L Dex-10 Medium (Donkersloot and Tarr, 1979, J. Clin. Microbiol., 10:919–922):
  trypticase 5 g
  yeast extract 5 g
  $K_2HPO_4\cdot 3H_2O$ 5 g
  $Na_2CO_3$ 50 mg
  glucose 1 g
  pH 6.8

Isolation of strains

Approximately 0.5 ml samples of soil or plant material were infused into 20 ml liquid culture media in 50 ml culture flasks and incubated 48 hours at 30° C. with agitation (250 rpm). Each sample was inoculated into four different media, LB, YEPD, Dex-10 without blue dextran and PMN with glucose substituted for lactose. Following incubation, aliquots of the liquid cultures were streaked or spread on each of the above-mentioned RBBA test media and incubated at 30° C. for 72–96 hrs until zones of activity appeared. Colonies showing zones of hydrolysis were determined to be capable of hydrolyzing alternan endo-hydrolytically and were restreaked for purity and to confirm activity on the dyed substrate.

For routine maintenance and for determination of enzymatic activity, cultures were grown in tryptic soy broth (17 g/L Bacto tryptone, 3.0 g/L Bacto soytone (Difco), 5.0 g/L NaCl, 2.5 g/L $K_2HPO_4$) supplemented with 0.25% glucose or alternan as the major carbon source at 30° C. and shaken at 250 RPM. Cultures were routinely transferred with a 1% inoculum and 96 hour cultures were used for enzymatic determinations.

In this experiment, seven strains of bacteria were isolated which produce and secrete extracellular alternanase. All seven strains have been deposited under the Budapest Treaty in the United States Department of Agriculture Agricultural Research Service culture collection in Peoria, Ill., and have been assigned deposit numbers NRRL B-21189, B-21190, B-21191, B-21192, B-21193, B-21194 and B-21195.

Characterization of strains

The seven soil isolates which were positive for alternanase activity were examined using standard protocols as outlined by Smibert and Krieg [1994, "Phenotypic Characterization", In: Methodology for General and Molecular Microbiology, P. Gerhardt (ed.), American Society for Microbiology, Washington, D.C., pp. 607–654]. Spores were harvested from cultures grown in Schaeffer sporulation media and suspensions were tested for heat resistance by heating to 80° C. for 10 min in a water bath. Spore viability was determined by plating on tryptic soy broth agar containing 0.5% RBBA. Strains NRRL B-21189, B-21190, B-21191, B-21192, B-21193, B-21194 and B-21195 were all found to be obligately aerobic, gram-negative bacilli, which produced heat resistant spores. All were catalase positive, oxidase negative, Voges-Proskauer negative, starch hydrolysis negative, and did not produce acid or gas from glucose. The seven strains were examined with the Biolog GP and GN Microplate Systems for their ability to utilize (oxidize) 95 different carbon sources. Dextrin, Glycogen Tween 40, $\alpha$-D-glucose, maltose, turanose, sucrose, D-trehalose, D-xylose, pyruvic acid, and fructose-6-phosphate were utilized by all seven strains. Fructose and inosine were utilized by all strains except NRRL B-21195, and gentibiose was utilized by all except NRRL B-21194. Although the strains have not been identified to species, all have been presumptively identified as belonging to the genus Bacillus, with the highest similarity to *Bacillus insolitus*.

EXAMPLE 2

*A. globiformis* NRRL B-4425 isomaltodextranase (E.C. 3.2.1.94) was purified according to the method described by Okada et al. (1988, Agric. Biol. Chem., 52:495–501) and assayed for endo-hydrolytic activity on both Remazol Brilliant Blue-alternan agar and liquid media as described in Examples 1 and 3, respectively. Because the enzyme did not liberate dyed fragments from the substrate, we concluded that the enzyme was not capable of endo-hydrolytic cleavage of alternan, and hence is not an alternanase.

EXAMPLE 3

Production of alternanase by strain NRRL B-21195, and the purification and properties of the enzyme, were further examined.

MATERIALS AND METHODS
Production of enzyme

Strain NRRL B-21195 from Example 1 was grown at 30° C. on a rotatory shaker (200 rpm) in a medium containing: Bacto Tryptone, 1.7%; Bacto Soytone, 0.3% (both from Difco Laboratories, Detroit, Mich.); NaCl, 0.5%; $K_2HPO_4$, 0.25% and 0.25% of the main carbohydrate source (selected from D-glucose, maltose, alternan, or starch). The strain showed very poor growth in a number of other media tested. Growth was followed by measuring the optical density of the cultures at 650 nm umedium inoculated medium as a reference. Dense cell suspensions were appropriately diluted with sterile non-inoculated medium.

Polysaccharides

Alternan and the Remazol-brilliant blue-alternan (RBBA) conjugate were prepared as described in Example 1. Nigeran and dextran B-512F were from obtained from Sigma Chemical Co., pullulan from Pfanstiehl (Waukegan, Ill.) and *Streptococcus sobrinus* 6715 dextran and *Leuconostoc mesenteroides* NRRL B-742 dextran, fraction S, were prepared as described by Cote and Robyt (1983, *Carbohydrate Res.*, 119:141–156; and 1984, *Carbohydrate Res.*, 127:95–107).

Determination of alternanase activity

In culture fluid with a large background of reducing sugars, alternanase activity was followed by use of RBBA as a substrate. The assay was based on determination of dyed fragments liberated from the substrate by the enzyme and remaining soluble after addition of ethanol. One volume of RBBA solution (5 mg/ml) in 0.05M sodium phosphate buffer (pH 7) was mixed with one volume of the cell-free culture fluid and incubated at 40° C. for various periods of time. The reaction was terminated by addition of two volumes of ethanol. Thoroughly mixed samples were left to stand at room temperature for 10 min, then centrifuged for 3 min at 14000 rpm in an Eppendorf centrifuge. Absorbance of supernatants was measured at 595 nm against substrate and enzyme blanks. Values of absorbencies of samples terminated at various times were plotted against time and the initial slopes of the curves were used to calculate the enzyme activity. The assay was calibrated with a reducing sugar assay, which was used as a more precise alternanase assay in samples with low backgrounds of reducing sugars. The assay was performed in 0.05M sodium phosphate buffer (pH 7) at a substrate concentration 2 mg/ml and a temperature of 40° C. One unit of alternanase activity is defined as the amount of enzyme that liberates the reducing equivalent of 1 $\mu$mol of D-glucose in 1 min.

To follow the enzyme in fractions collected during chromatographic and electrophoretic purification of the enzyme, a cup-plate semiquantitative procedure was used, suggested first for endo-$\beta$-1,4-glycanases by Biely et al. (1985, *Anal. Biochem.*, 144:147–151) and Kluepfel (1988, *Methods Enzymol.*, 160:180–186). A hot solution of 0.3% RBBA, 0.02% sodium azide and 2% agar (Difco) in 0.025M sodium phosphate buffer was poured into Petri dishes, left to solidify and subjected to well cutting. Enzyme solutions were pipetted to wells, left to incubate in a chamber at 100% relative humidity and 40° C. and observed for destaining around the wells as a sign of the enzyme presence. Diameter of the destained area is in a linear relationship with the logarithm of the enzyme concentration.

Size-exclusion chromatography

Proteins were fractionated on a column of hydrophilic bonded silica (BioSep-SEC-S3000, 300×7.5 mm, Phenomenex, U.S.A.), eluted at 350 psi with 50 mM sodium Hepes (N-2-hydroxyethylpiperazine-N'-2-ethanesulfonic acid, Research Organics, Inc., Cleveland, Ohio, U.S.A.) buffer (pH 7.5) containing 50 mM NaCl, 2 mM $CaCl_2$ and 5 mM $NaN_3$, at a rate of 0.7 ml/min, (Waters 650E Advanced Protein Purification System). Protein was monitored at 280 nm and alternanase either by the cup-plate assay (see above) or by reducing sugar assay.

Electrophoretic methods

Polyacrylamide gel electrophoresis (PAGE) was performed according to Laemmli (1970, Nature, 227:680–685, the contents of which are incorporated by reference herein), both in the presence and in the absence of SDS, in a vertical slab gel unit (SE 600, Hoefer Scientific Instruments, San Francisco). Analytical separations were done in gels of 1 mm thickness, preparative in gels of 2.5 or 3 mm thickness. After location of alternanase by the zymogram technique described below, the enzyme-containing band of the gel was cut out and subjected to electroelution (ISCO electroelutor/concentrator, ISCO, Inc. Lincoln, Nebr., U.S.A.) at 1 watt setting for 16 h at 4° C. The dialysis membranes were prepared as recommended by Bhown et al. (1980, Anal. Biochem., 103:184–190). Tris-acetic acid buffer, pH 8.6, was used at the following concentrations: 0.04M in the electrode compartments, 0.01M in the inner chambers and 0.005M in the sample cup. Eluted protein was removed from the bottom of the cup in 0.2 ml fractions that were assayed for alternanase activity by the cup-plate method. Fractions containing the enzyme were pooled, concentrated and desalted (Centricon-10 concentrators, Amicon, Inc., Beverly, Mass., U.S.A.), and finally freeze-dried. Analytical isoelectric focusing was performed on ready-made minigels (PhastSystem, Pharmacia, Sweden). In all cases, proteins were made visible with silver nitrate as described by Giulian et al. (1983, Anal. Biochem., 129:277–287).

Location of alternanase in gels

The zymogram technique used was similar to that developed for the detection of endo-β-1,4-glucanases and endo-β-1,4-xylanases (Biely et al., 1985, ibid). A gel with proteins resolved by PAGE under native conditions was washed twice in 0.1M sodium phosphate buffer for 10 min, brought into contact with 1% agarose detection gel containing 0.5% RRBA in 0.025M sodium phosphate buffer (pH 7), and then incubated in a wet chamber at 40° C. until a change of the blue background was observed where alternanase hydrolyzed the blue substrate. The detection gel was then separated from the separation gel and gently shaken overnight in ethanol-0.05M sodium acetate buffer, pH 5, (2:1, v/v) to destain the area where the substrate was digested.

Other methods

Reducing sugars were determined by the Somogyi-Nelson procedure as described by Paleg (1959, Anal. Chem., 31:1902–1904) and proteins using the BioRad protein assay of Bradford (1976, Anal. Biochem., 72:248–254). Products of alternan hydrolysis were analyzed by thin-layer chromatography on silica gel precoated plates (Merck, Darmstadt, Germany) irrigated with nithroethane-acetonitrile-ethanol-water (1:4:3:2, v/v). Reducing sugars were detected with diphenylamine-aniline-phosphoric acid reagent as described by Bailey and Bourne (1960, J. Chromatogr., 4:206–213) and all carbohydrates with N-(1-naphthyl)ethylenediamine dihydrochloride reagent as described by Bounias (1980, Anal. Biochem., 106:291–295).

RESULTS AND DISCUSSION

Production of alternanase by Bacillus NRRL B-21195

The strain was grown on four different structurally related carbon sources, D-glucose, maltose, starch and alternan, and growth, extracellular protein and extracellular alternanase activity were measured during the course of the fermentation. The data from the starch medium were very similar to those obtained in the medium with maltose. The strain grew faster and gave much larger growth yields on maltose and alternan than on D-glucose. However, the fast growth rate was accompanied by intense cell lysis, reflected in the drop of absorbance of the cell suspensions and marked increase of extracellular protein in cell-free medium after about 50 h. The enzyme production was comparable on all carbon sources tested, suggesting that in this species alternanase is a constitutive enzyme. This is a feature by which NRRL B-21195 differs from other alternanase-producing bacterial isolates which require alternan in the growth medium to produce appreciable levels of enzyme activity. A comparison of the extracellular levels of alternanase and protein on various carbon sources points to the fact that the specific activity of alternanase in the culture fluid is highest in the D-glucose medium.

Electrophoretic analysis of the extracellular proteins from the D-glucose and alternan cultures showed that the bacterium always produces only one form of alternanase. These were the main reasons why the enzyme purification was started from a D-glucose culture. An additional reason was that preliminary examination of the enzyme activities in the various media revealed that on D-glucose, in contrast to other carbon sources tested, the strain did not produce significant quantities of other enzymes hydrolyzing α-D-glucopyranosyl linkages that could complicate the enzyme purification. Whereas the compositions of alternan hydrolyzates with purified enzyme and with a crude enzyme from the D-glucose medium were almost identical, the alternan-induced crude enzyme preparation hydrolyzed alternan to a greater extent and to smaller molecular mass products, including D-glucose.

Purification of alternanase

A 4-day old culture on D-glucose was centrifuged and the cell-free supernatant, after being supplemented with 0.02% $NaN_3$, was concentrated to 5% of its original volume and desalted (Amicon DC-2 Hollow Fiber Concentrator). About 85% of the total alternanase activity present in the concentrate was precipitated from the medium at 40% saturation with ammonium sulfate. The precipitated protein was collected by centrifugation (100,000×g, 30 min) and dissolved in the smallest possible volume of water. This step led to 2.5-fold purification of the enzyme. Dialyzed protein was subjected in portions to size exclusion chromatography as described hereinabove. Protein was separated into four distinct fractions, one of which contained all alternanase activity. This step resulted in an additional 2.5-fold increase in specific activity of the enzyme. The fractions with the highest activity were pooled, concentrated and desalted by ultrafiltration, and subjected to ion-exchange chromatography on a Millipore Mem Sep 1010 DEAE module, using a gradient of NaCl. Alternanase was eluted from the column as a sharp peak at about 0.3M NaCl, together with many other proteins, and its specific activity increased from the previous step by only about 10%. Therefore, this step was omitted in further purification of the enzyme. The size exclusion chromatography fraction was subjected to preparative PAGE. Care was taken that no more than 0.5 mg of alternanase protein was loaded on one gel consisting of 10 ml of stacker gel and 54 ml of the running gel. After location of alternanase with RBBA-agarose gel, the band containing the enzyme was precisely cut from the separation gel and the enzyme was obtained by electroelution. A summary of the purification starting from 1 liter of D-glucose culture is given in Table 1. The individual steps of purification were monitored by PAGE under native conditions. The final preparation that showed specific activity of approximately 1.2 U/mg of protein gave essentially a single protein band on both native and SDS-PAGE. More sensitive detection of protein with silver nitrate revealed the presence of a tiny accompanying protein band migrating in front of the main band but always in close association. The minor band must be related to the major form of alternanase because it shows alternanase activity on RBBA zymograms. Purity of the final enzyme preparation was also confirmed by determination of several amino acid sequences, including the N-terminal one.

Properties of purified alternanase

The molecular mass of the purified alternanase was determined by SDS-PAGE. Enzyme boiled in the presence of SDS shows a molecular mass of 110 kDa. Removal of SDS from the gel by two successive 15 min washings in 0.1M sodium phosphate buffer (pH 7) led to a partial renaturation of alternanase as shown by activity on RBBA. The enzyme apparently did not unfold completely in SDS solution without heating at 100° C. Under such conditions it showed a much lower molecular mass. The alternanase protein must be quite densely packed because the enzyme was eluted from the size exclusion column as though it were a 60 kDa protein.

The isoelectric point of the enzyme as determined by isoelectric focusing is approximately pH 4. Again, only one molecular form of the enzyme was apparent by this method.

The pH optimum was examined in sodium phosphate buffers adjusted to desired pH values. Alternanase showed maximum activity at pH 7. The temperature optimum at pH 7 was 40° C. At 50° C., the reaction was diminished by about 50%. This observation was interesting relative to the results on temperature stability of the enzyme. Alternanase was quite stable at 50° C. and lost activity rapidly at 60° C. At 50° C. the enzyme probably changed its conformation reversibly, so that a complete recovery of enzyme activity was achieved on cooling to 40° C.

Results from the determination of the amino acid composition of alternanase are shown in Table 2. However, cysteine and tryptophan may also be present in the enzyme, but their presence cannot be determined using the analytical procedure employed herein.

Effect of ions

Effects of selected cations on alternanase activity were examined in the presence and in the absence of 0.1M EDTA. As shown in Table 3, the enzyme was severely inhibited by $Hg^{2+}$, which suggests the presence and importance of sulfur-containing amino acids. $Ca^{2+}$ was the only cation that stimulated enzyme activity in the absence of EDTA. In the presence of EDTA, when all calcium ions can be assumed to be bound by EDTA, addition of $Ca^{2+}$ enhanced the alternanase activity more than two-fold. The inhibitory effect of EDTA was eliminated by $Ca^{2+}$ ions at concentrations exceeding that of EDTA.

Substrate specificity

Table 4 lists the initial rates of hydrolysis of various α-D-glucans, at 0.2% concentration, by purified alternanase, measured by determination of reducing sugars. Alternan is the best substrate for the enzyme, however, low initial rates of hydrolysis were recorded in the cases of pullulan and, to a lesser extent, starch. In both instances, early cessation of hydrolysis suggested that both polysaccharides contain only limited numbers of linkage sequences that are attacked by alternanase. Also, since the hydrolysis of pullulan and starch is unlikely to result in the formation of the cyclic oligosaccharides, the relative rates of hydrolysis of these glucans are probably even less than the data in Table 4 suggest. That the enzyme had no action on dextrans and some related polysaccharides indicates that alternanase is a new type of endoglucanase specific for α-D-glucans in which α(1→3) and α(1→6) linkages alternate.

Evaluation of the extent of hydrolysis of alternan by determination of liberated reducing sugars pointed to low extent of hydrolysis, as if less than 10% of all glycosidic linkages were cleaved. The crude enzyme from the D-glucose medium gave somewhat higher values. Thin-layer chromatography of alternan digested with the purified enzyme, applying two different detection procedures, showed that two major products in the digest are non-reducing, or at least do not react with the diphenylamine/aniline/phosphoric acid reagent as readily as some of the reducing products. That isomaltose but neither nigerose nor D-glucose were among the reducing products suggested that the α-1,3-linkage is the target of the enzyme.

EXAMPLE 4

MATERIALS AND METHODS

Enzymes and substrates

Purified alternanase was obtained from the culture fluid of Bacillus NRRL B-21195 as described in Example 3. One unit of enzyme activity was defined as the amount releasing one μmole of reducing sugar per minute from alternan at 40° C. Alternan was synthesized as described in Example 3, and was extensively dialyzed to remove residual low-molecular-mass sugars. *Arthrobacter globiformis* NRRL B-4425 isomaltodextranase was prepared as described in Example 2. Glucoamylase from *Aspergillus niger* (EC 3.2.1.3) was purchased from Boehringer Mannheim.

Analytical methods

Total carbohydrate was determined by the phenol-sulfuric acid method described by Dubois et al. (1956, *Anal. Chem.*, 28:350–356). Reducing sugar values were measured by the Somogyi-Nelson copper reduction procedure as described by Somogyi (1952, *J. Biol. Chem.*, 195:19–23). Maltose solutions were used as standards in both procedures. Partial acid hydrolysis was accomplished with 1M trifluoroacetic acid at 100° C. for 20 minutes. Thin layer chromatography employed Whatman K5 silica gel plates irrigated for two ascents in the solvent system consisting of nitroethane-acetonitrile-ethanol-water (1:4:3:2, v/v.). Carbohydrates were made visible with N-(1-naphthyl)ethylenediamine dihydrochloride reagent as described by Bounias (1980, ibid). Proton and $^{13}$C-NMR spectroscopy measurements on samples dissolved in $^2H_2O$ were made by use of Bruker ARX spectrometer equipped with a 5 mm $^1$H/$^{13}$C dual probe, at 400.13 MHz ($^1$H) and 100.61 MHz ($^{13}$C). Methylation analyses were done according to published procedures by Seymour et al. (1977, *Carbohydr. Res.*, 53:153–166). Chemical ionization mass spectrometry was carried out in a Finnegan TSQ 700 instrument, with ammonia as the reagent gas. Fourier-transform infrared spectra were obtained from pressed KBr pellets, with a KVB-Analect RFX-75 spectrometer and TGS detector at 4 $cm^{-1}$ resolution. Optical rotations were measured at 25° C. on samples dissolved in distilled water (Perkin Elmer model 241 polarimeter).

Preparation of oligosaccharides

Twenty-five (25) mL of an 8% (w/v) solution of alternan in water containing 0.02% sodium azide was treated with approximately 0.06 units of alternanase at 40° C. for 5–6 days. Progress of the hydrolytic reaction was monitored by thin-layer chromatography. Undigested polysaccharide was precipitated by the addition of two volumes of ethanol and then centrifuged. The supernatant solution was concentrated by rotary evaporation at 40° and lyophilized. The residue was dissolved in water, and component saccharides were separated by preparative high-performance liquid chromatography (HPLC) on a 10×250 mm amino column (Rainin Dynamax 60A, 8 μm particle size). Acetonitrile-water (7:3 v/v) at a flow rate of 4 mL $min^{-1}$ was used as the mobile phase. Detection was by refractive index (Waters model R401detector). Fractions of 4 mL each were collected and analyzed by thin layer chromatography, and those that contained the compounds of interest were combined, concentrated by rotary evaporation, and lyophilized.

RESULTS

Mono-, di-, and trisaccharides

Thin layer chromatography of the products of enzymatic alternan degradation with purified alternanase showed that neither glucose nor nigerose were formed at any time. Glucose was produced in addition to oligosaccharides, however, when crude or partially purified alternanase preparations were used. There is apparently an α-D-glucosidase activity present that is removed by purification. At least eight separate products were discernable by TLC. HPLC of the portion of the digest that remained soluble after addition of ethanol was unable to completely resolve compounds V–VII. In the HPLC profile, D-glucose and isomaltose were the first components eluted. Several higher oligosaccharides were also produced. The third compound eluted, upon isolation and reducing sugar analysis, proved to be a reducing trisaccharide. This was confirmed by chemical ionization mass spectrometry of the permethylated compound. Analysis of the partial acid hydrolyzate of this compound by thin layer chromatography showed glucose, nigerose, and isomaltose. $^{13}$C-NMR analysis revealed the presence of both α(1→3) and α(1→6) linked residues. The trisaccharide ($[\alpha]_D^{25}$+151°) was hydrolyzed completely to D-glucose by glucoamylase. Resistance to hydrolysis by isomaltodextranase eliminated the possibility of α-D-glucopyranosyl-(1→6)-α-D-glucopyranosyl-(1→3)-D-glucose, which would have been hydrolyzed to D-glucose and isomaltose [24]. Methylation analysis yielded equimolar quantities of the 2,3,4- and 2,4,6-tri-O-methyl and 2,3,4,6-tetra-O-methyl per-O-acetylated aldononitrile derivatives of D-glucose (Table I). Therefore, the structure of the trisaccharide produced from alternan must be α-D-glucopyranosyl-(1→3)-α-D-glucopyranosyl-(1→6)-D-glucose.

Cyclic tetrasaccharide

The product formed in the largest relative proportion by alternanase action on alternan was the fourth compound (peak IV) eluted during HPLC. The purified compound ($[\alpha]_D^{25}$+214°) migrated on TLC ahead of isomaltotriose, but behind panose and the trisaccharide. Its reducing value was negligible. Crystals of oligosaccharide IV, obtained from methanol-water solution, decomposed without melting above 250° C. The $^1$H-decoupled $^{13}$C-NMR spectrum contained twelve signals, including two signals of equal intensity in the C-1 anomeric region. No NMR peaks attributable to a reducing end C-1 were seen. Likewise, the $^1$H-NMR spectrum displayed only two anomeric proton signals, of equal intensity. Table 5 summarizes the NMR data. The FT-IR spectrum contained a sharp peak at 796 cm$^{-1}$, characteristic of the α(1→3) linkages found in alternan (Seymour and Julian, 1979, Carbohydr. Res., 74:63–75). Methylation analysis yielded equimolar quantities of 2,3,4- and 2,4,6-tri-O-methyl per-O-acetylated glucononitrile (Table 6). Chemical ionization-mass spectrometry of the per-O-methylated oligosaccharide showed an (M+NH$_4^+$) ion peak with a m/z ratio of 834.7, for an apparent mass of 816.7 for the per-O-methylated oligosaccharide. Oligosaccharide IV was not hydrolyzed by glucoamylase, but treatment with isomaltodextranase resulted in its complete conversion to isomaltose. During isomaltodextranase hydrolysis of IV, there was transient formation of a slower-migrating compound, which likely represented a reducing tetrasaccharide formed by hydrolysis of one of the α(1→3) linkages of compound IV. The hydrolytic reaction products arising from compound IV are shown in Cote and Biely (1994, ibid). These results show oligosaccharide IV to be the cyclic tetrasaccharide cyclo{→6)-α-D-Glcp-(1→3)-α-D-Glcp-(1→6)-α-D-Glcp-(1→3)-α-D-Glcp-(1→}.

Higher oligosaccharides

The compounds migrating between peaks IV and VIII on TLC were not completely resolved by HPLC. The structures of these relatively minor products have not yet been determined. Compound VIII was isolated by HPLC, and methylation analysis was performed as above. Chemical-ionization mass spectrometry of the per-O-methylated compound showed an (M+NH$_4^+$) ion peak at m/z=1038.8, and GLC-MS analysis of the per-O-acetylated methylated aldononitrile derivatives after hydrolysis and derivatization gave the results shown in Table 6. These data indicate a glucosylated cyclic tetrasaccharide having a single D-glucopyranosyl unit attached to O-6 of one of the 3-O-glucosylated ring residues. The $^{13}$C-NMR spectrum for compound VIII is consistent with this structure. Glucoamylase slowly hydrolyzed compound VIII to D-glucose plus compound IV (identified by TLC mobility). Compound VIII was hydrolyzed by isomaltodextranase to isomaltose and trisaccharide III. Partial acid hydrolysis yielded a mixture of saccharides, including D-glucose, compound IV, and isomaltose. Alternanase also slowly hydrolyzed compound VIII to isomaltose and trisaccharide III as well as to a compound migrating more slowly than VIII on TLC. This slower-migrating compound was completely degraded by isomaltodextranase to isomaltose and trisaccharide III, and is believed to be an open-chain form of VIII.

The oligosaccharide produced in the greatest proportion was the cyclic tetrasaccharide IV. Preliminary computer modeling studies using Chem-X and MM3 indicate that the cyclic structure is unstrained. We have succeeded in crystallizing the compound. Of special interest is the $^{13}$C-NMR spectrum of the cyclic tetrasaccharide. The glycosylated C-3 resonance appears at 76.9 ppm, whereas a typical value for a substituted C-3 in a non-cyclic D-glucooligosaccharide (e.g., nigerose) would be in the range of 80–83 ppm (Usui et al., 1973, J. Chem. Soc. Perkin, I:2425–2432). Bock et al. (1986, J. Chem. Soc. Perkin, II:1711–1713) have shown that the magnitude of the downfield shift in the $^{13}$C signal upon glycosylation depends on the glycoside bond torsion angle ψ. The glycosylated C-3 in compound IV exhibits a downfield shift of 1.8 ppm relative to that of the unsubstituted C-3 in the same compound (Table 6). According to the equation derived empirically by Bock et al., this would suggest a ψ angle of −47.7°. Conformational modelling using MM3 indicates that the least strained conformation of compound IV may be asymmetric, possessing α(1→3) linkages with ψ angles of −47.9° and −37.5°.

Several other oligosaccharides were produced in addition to the trisaccharide III and cyclic oligosaccharide IV. That formed in the largest proportion, compound VIII, is an α-D-glucosylated, or "branched", derivative of IV in which the additional D-glucose residue is attached to the cyclic tetrasaccharide through an α(1→6) linkage. Compound V, which was formed as a minor component, has been isolated in small amounts. It should be noted that, although significant amounts of V were formed by crude or partially purified alternanase, scarcely any was detected when pure enzyme was used. Preliminary methylation and NMR studies indicate that compound V is a positional isomer of VIII, in which the cyclic tetrasaccharide is D-glucosylated through an α(1→4) linkage. It is believed that compound V represents a reversion or condensation product of glucose and oligosaccharide IV formed by a contaminating α-D-glucosidase; this is supported by the fact that scarcely any V was detected on TLC when pure enzyme preparations were used. Of course, the possibility that alternanase itself may be capable of forming (1→4) linkages cannot be discounted.

The observations that alternanase hydrolyzes both RBBA and the cyclic oligosaccharide IV are strong evidence in support of an endolytic mode of action. The cyclic oligosaccharides that accumulate in the enzymic digests predominate throughout the course of the reaction. Once isolated, however, they are slowly degraded by alternanase. Thus, they are not end-products per se, but represent structures that are formed more readily than they are cleaved, and therefore predominate at equilibrium. It may be that some of the oligosaccharide products inhibit the enzyme.

It is understood that the foregoing detailed description is given merely by way of illustration and that modifications and variations may be made therein without departing from the spirit and scope of the invention.

TABLE 1

Summary of the purification of extracellular alternanase

| Step | Volume (mL) | Protein (mg/mL) | Protein (mg) | Alternanase (U/mL) | Alternanase (U) | Spec. activity (U/mg) | Purification (degree) | Yield % |
|---|---|---|---|---|---|---|---|---|
| Culture fluid concentrate* | 35 | 1.4 | 49 | 0.15 | 5.3 | 0.11 | 1 | 100 |
| $(NH_4)_2SO_4$ precipitate | 2 | 8.5 | 17 | 2.30 | 4.6 | 0.27 | 2.5 | 87 |
| Size-exclusion chromatography | 17 | 0.2 | 3.4 | 0.15 | 2.5 | 0.75 | 6.8 | 47 |
| Prep. PAGE | 0.5 | 0.45 | 0.22 | 0.52 | 0.26 | 1.18 | 10.7 | 5 |

*From 900 mL cell-free culture fluid

TABLE 2

Amino Acid Composition of B-21195 Alternanase

| Amino Acid* | Mole % |
|---|---|
| Asx** | 10.6 |
| Glx*** | 9.2 |
| Ser | 8.7 |
| Gly | 8.6 |
| His | 2.1 |
| Arg | 3.2 |
| Thr | 7.3 |
| Ala | 10.3 |
| Pro | 5.4 |
| Tyr | 7.3 |
| Val | 4.7 |
| Met | 2.7 |
| Ile | 3.9 |
| Leu | 7.4 |
| Phe | 4.4 |
| Lys | 4.2 |
| TOTAL | 100 |

*Cys and Trp not included in analysis
**Asx = asp or asn
***Glx = glu or gln

TABLE 3

Effect of cations and EDTA on alternanase activity under standard assay conditions

| Addition (1 mM) | Relative Activity EDTA Absent | Relative Activity 0.1 mM EDTA Present |
|---|---|---|
| None | 100 | 71 |
| $Ca^{2+}$ | 148 | 158 |
| $Cu^{3+}$ | 69 | 70 |
| $Fe^{3+}$ | 18 | 39 |
| $Fe^{3+}$ | n.d* | 77 |
| $Hg^{2+}$ | 6 | 19 |
| $Mg^{2+}$ | 83 | 90 |
| $Mn^{2+}$ | 25 | 65 |
| $Zn^{2+}$ | 88 | 60 |
| EDTA | 19 | n.d* |

*Not determined

TABLE 4

Substrate specificity of purified alternanase acting on various α-D-glucans
Polysaccharide solutions (0.2% in 0.1 M sodium phosphate buffer, pH 7) were incubated with enzyme at 4° C. and initial velocities were measured as reducing sugars released over time.

| Polysaccharide | Glycosidic linkages present | Relative initial rate of hydrolysis (%) |
|---|---|---|
| Alternan | α(1-3) azida(1-6) (alternating) | 100 |
| Pullulan | α(1-4) and α(1-6) (2:1 ratio) | 9* |
| Soluble starch | α(1-4) with α(1-6)branches | 3* |
| Nigeran | α(1-3) and α(1-4) (alternating) | <1 |
| Dextran (B-512F) | α(1-6) with α(1-3) branches (~5%) | <1 |
| Dextran (B-742 fr. S) | α(1-6) with α(1-3) branches (~28%) (·8% α(1-4) branches also present) | <1 |
| Dextran (*Streptococcus sobrinus* 6715) | α(1-6) with α(1-3) branches(~33%) | <1 |

*Hydrolysis proceeds to very low extent only.

TABLE 5

Chemical shifts and coupling constants for Compound IV
(cyclic D-gluocotetrasaccharide)

|  | Carbon No. | $^{13}C$ (ppm) | $^{1}H$ (ppm) | Coupling constants (Hz) |
|---|---|---|---|---|
| 6-O-glycosylated | 1 | 99.0 | 5.68 | $J_{1,2} = 3.9$ |
| residues | 2 | 74.0 | 3.62 | $J_{2,3} = 9.8$ |
|  | 3 | 75.1 | 3.8 | $J_{3,4} = 9.0$ |
|  | 4 | 73.0 | 3.31 | $J_{4,5} = 10.1$ |
|  | 5 | 72.5 | 4.49 |  |
|  | 6 | 69.9 | 3.8 |  |
| 3-O-glycosylated | 1' | 100.8 | 4.98 |  |
| residues | 2' | 72.3 | 3.68 | $J_{1',2'} = 9.8$ |
|  | 3' | 76.9 | 4.12 | $J_{3',4'} = 9.0$ |
|  | 4' | 73.3 | 3.74 | $J_{4',5'} = 9.6$ |
|  | 5' | 73.9 | 3.8 |  |
|  | 6' | 62.5 | 3.8 |  |

TABLE 6

Methylation analyses. Relative molar ratios of per-O-acetylated
D-glucononitrile derivatives from per- O-methylated
oligosaccharides. Data are normalized relative to the 2,4,6-tri-O-methyl derivative.

| Compound | 2,3,4,6-tetra-O-methyl | 2,3,4-tri-O-methyl | 2,4,6-tri-O-methyl | 2,4,-di-O-methyl |
|---|---|---|---|---|
| III | 1.2 | 0.9 | 1.0 | 0.0 |
| IV | 0.0 | 1.0 | 1.0 | 0.0 |
| VIII | 1.2 | 2.2 | 1.0 | 1.2 |

We claim:

1. A substantially pure cyclic tetrasaccharide having the structure:

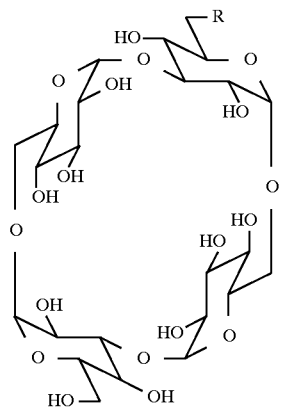

wherein R is a D-glucopyranosyl residue or —OH; or derivatives thereof.

2. The cyclic tetrasaccharide of claim 1 wherein said R is —OH.

3. The cyclic tetrasaccharide of claim 1 wherein said R is a D-glucopyranosyl residue.

4. The cyclic tetrasaccharide of claim 1 wherein said derivatives are selected from the group consisting of O-alkyl ethers, O-acyl esters, partially or fully sulfated esters, and ionic carboxymethyl and diethylaminoethyl derivatives.

5. The cyclic tetrasaccharide of claim 1 which is substantially pure.

* * * * *

UNITED STATES PATENT AND TRADEMARK OFFICE
CERTIFICATE OF CORRECTION

PATENT NO. : 5,889,179
DATED : Mar. 30, 1999
INVENTOR(S) : Gregory L. Cote and Peter Biely It is certified that error appears in the above-identified patent and that said Letters Patent is hereby corrected as shown below:

On the title page item [54],

"Alternant" should be "Alternan".

The Inventors listed are incorrect they are listed as:
Gregory L. Cote, Edwards; Herbert Wyckoff, Washington, both of Illinois.
The Inventors should be listed as:
Gregory L. Cote, Edwards, Illinois; Peter Biely, Bratislava, Slovakia.

Signed and Sealed this

Fourteenth Day of September, 1999

Attest:

Q. TODD DICKINSON

*Attesting Officer*    *Acting Commissioner of Patents and Trademarks*